April 13, 1971 H. A. JOHNSON, JR., ET AL Plant Pat. 3,042
STRAWBERRY PLANT
Filed June 11, 1969
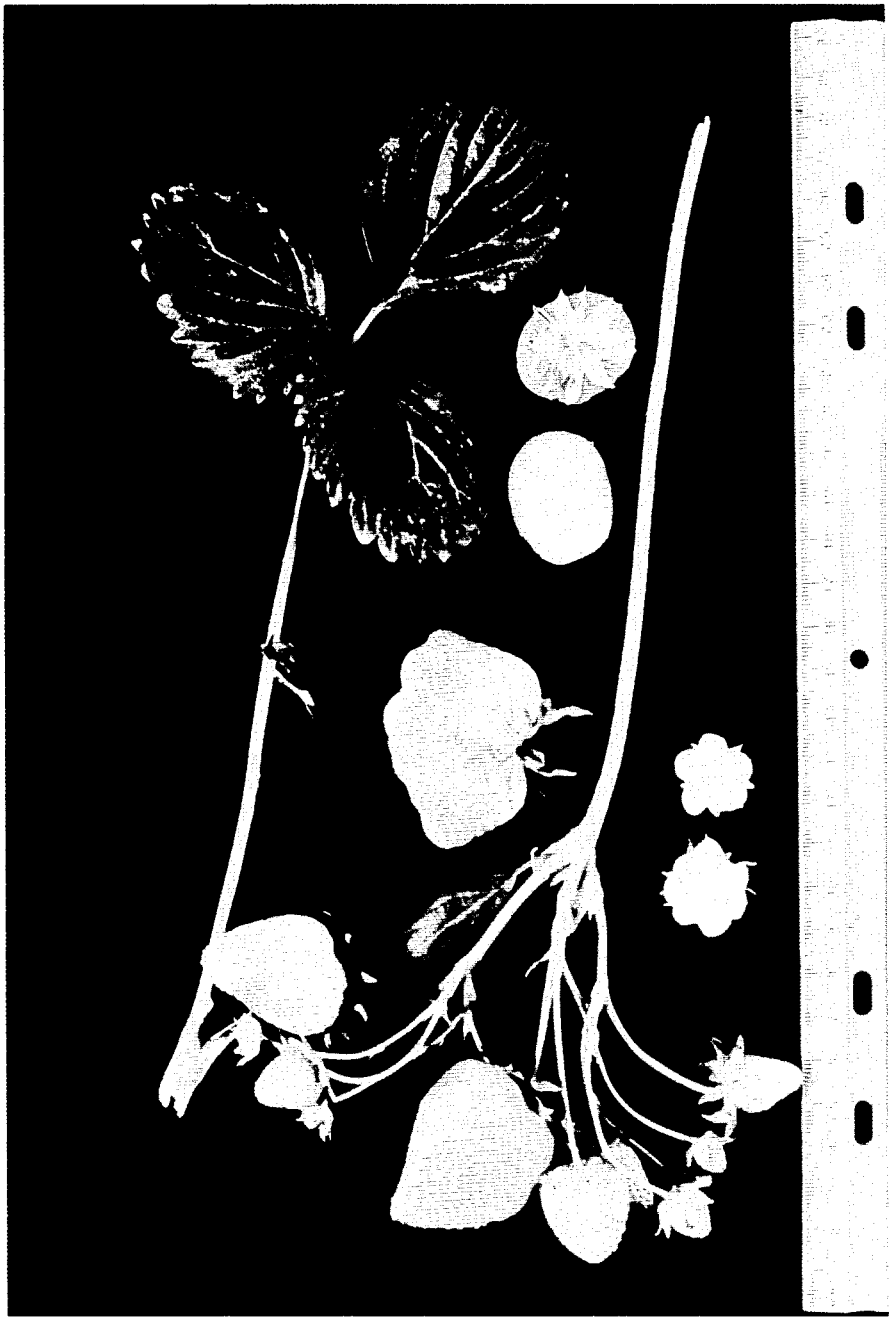
INVENTORS
HAROLD A. JOHNSON, JR.
HAROLD E. THOMAS
BY
Townsend and Townsend
ATTORNEYS United States Patent Office Plant Pat. 3,042
Patented Apr. 13, 1971

3,042
STRAWBERRY PLANT

Harold A. Johnson, Jr., and Harold E. Thomas, Watsonville, Calif., assignors to Driscoll Strawberry Associates, Inc., Watsonville, Calif.

Filed June 11, 1969, Ser. No. 832,510
Int. Cl. A01h 5/03
U.S. Cl. Plt.—49 1 Claim This invention relates to a novel and distinct variety of strawberry plant which is the result of a cross of the unpatented everbearing variety known as The Strawberry Institute of California selection No. F121.7 and the variety disclosed in Goldsmith Pat. No. 1,735 issued July 29, 1958.

The seedlings resulting from the aforementioned cross were grown and asexually reproduced in Shasta County, California, and tested in the fruiting beds on the property of growers of the Driscoll Strawberry Associates, Inc. Clones of these seedlings were also held at the Propagation Nursey in Shasta County. One plant was selected from the aforementioned group of seedlings, and further asexual reproduction was performed in the Shasta County nursery of Driscoll Strawberry Associates, Inc. Tests followed in various parts of California during intervening seasons on various properties of grower members of the Driscoll Strawberry Associates, Inc. These tests indicated the merit of this novel plant and resulted in its selection as a promising test variety.

Parts of a plant of the new variety, typical in size, shape and color are pictured in the accompanying drawing in which a typical inflorescence is pictured with one ripe primary berry attached, plus a partially ripened secondary berry. In the same drawing a wedged shaped berry is pictured. To exemplify flesh color and core cavity another berry is shown in cross section. A typical leaf and two primary flowers are also pictured in the drawing.

The plant is medium in size, becoming larger and vigorous in the later part of the season. Multiple crowns are produced by the end of the first year and the plant may become dense by the end of the second year. It is an everbearing variety in that it may be planted during the spring or winter while still yielding a crop during the first growing year. The novel plant is a high producing variety with only small fruit coming from the crown crop. The primaries produced by the first main crop are large and showy berries. Secondary and tertiary fruit is smaller and as the season progresses the average fruit size decreases. If the plants are planted in January or early February, the first main crop appears during the last days of May or the first days of June. Production continues until the end of August with some production continuing until frost or rain in the fall of the year.

This novel variety is distinguished by its flowers, fruit and plant characteristics. In general, the plant of this new variety may become as large or larger than the Goldsmith variety. The plant is distinct from the Goldsmith variety in that it may become denser. The leaves are longer, darker and more glossy. The inflorescences are more abundant and many flowers are visible above the plant, especially during the early summer period. Most of the new leaves on this new variety are glossy and are not rugose at first but may become so as the leaves age. The leaflet serrations are distinct from those found on the Goldsmith variety in that they are not as deep nor is their apex as acute. Central leaflets are usually longer than they are wide. As pictured in the drawing, the petiolule of the new variety is noticeably long, usually even longer than that found on the Goldsmith variety. Bracts are often found on the petioles. The inflorescences of this novel variety are abundant, but generally not as long as those of the Goldsmith variety.

The main common peduncle is noticeably long in contrast to the secondary peduncles. Individual inflorescences often produce more than two secondary peduncles with as many as five being not uncommon. The pedicel holding the primary berry of most inflorescence originates mainly from one of the peduncles as is pictured in the illustration. Occasionally this pedicel originates from the axil formed by the union of peduncles. The pubescence on the tertiary pedicles is equal to Goldsmith in amount and in the way it lays against the pedicles.

The fruit of this new variety is quite distinct in its appearance and outline. Its color is bright, glossy and usually dark, often with a white area around the calyx. Most berries are distinctly wedged in outline with primaries often becoming wedged and at times having a cockscomb apex as shown in the drawing. A percentage of the berries may be irregularly conic in outline and some may have longitudinal furrows extending the full length of the fruit.

The calyx is large and showy, usually held in a reflexed position when attached to the fruit. Individual sepals may be serrated and are wider and less elliptical than those of the Goldsmith variety. The seed becomes quite dark on the exposed side of the fruit and is held equal to or slightly below the fruit surface. The epidermis of this fruit is generally firm, but may become weak during certain periods of the fruiting year. This may occur especially at the apex of the cockscomb type wedge shaped fruit. Secondary and tertiary berries late in the season may also have weak skin. Albino berries are common in this variety. The flesh is generally firm at other times. There is generally a more solid core, a higher sugar content and better dessert quality in this novel variety than found in berries of the Goldsmith variety. It is an abundant runner producer. This novel variety is equal to Goldsmith in its resistance to the Two-Spotted Mite and Powdery Mildew. It is susceptible to Verticillium Wilt, Cyclamen Mite and Red Stele. As a seedling this novel variety withstood the natural invasion of the virus components found in central California without losing its ability to produce.

The varietal characteristics of the new plant, described below in detail, were observed during the first fruiting season. Observations were made in the Watsonville area of California which is a cool coastal area near the Pacific Ocean. The color terminology is in accordance with Ridgway's Color Standards and Nomenclature (1912 Edition).

*Plant.*—Is medium in size, becomes denser and multiple crowned during the first and second years with a strong root system.

*Leaves.*—Are medium in size. The central leaflet is usually 5.5 to 7.5 cm. in diameter and their length is greater than their width. The leaflet margins are slightly cupped upward. The leaflet surface is mostly glossy and not rugose, but with age they may become slightly rugose. The serrations at the margins are shallow and rounded at the apex. The leaflet upper side color at Watsonville in July is Dusky Yellowish Green, Plate XLI.

*Runners.*—Are abundant and vigorous at the nursery but are moderate in fruiting beds.

*Inflorescence.*—Is medium in length, may produce 2 to 5 secondary peduncles per inflorescence. The pedicel holding the primary berry usually originates from a secondary peduncle, but may originate from the axil formed by the union of the peduncles. Flower anthers produce an abundance of pollen even under cold, wet and windy conditions. Flowers are conspicuously visible above the plant. Hair on the tertiary pedicles, 20 mm. below the flower, lays against and is parallel with the pedicel.

*Fruit.*—Crown crop berries are small, but primaries from first main crop are large, glossy and attractive, 35 to 45 mm. in length with width usually equal to the length. The fruit becomes smaller as the season progresses. The primaries are irregular wedged to conic in shape with many primaries having a cockscomb outline with several acute apexes. One or more of the apexes may lack full red color. Skin and flesh are usually firm; the fruit core is small. The outside color of the fruit is glossy and dark, Oxblood Red to Carmine, Plate I. Flesh color is White to Nople Red, Plate I.

*Calyx.*—Is large; the calyx of most primary berries is 35 to 45 mm. The sepals are large and abundant, generally overlapping each other and deeply serrated at the apex. Sepals of secondary and tertiary berries may be elliptical in outline but the sepals of primaries are wider, especially at the point where they are attached to the pedicel.

We claim:

1. The new and distinct variety of strawberry plant herein described and illustrated, and identified by the characteristics enumerated above.

No references cited.

ROBERT E. BAGWILL, Primary Examiner